US011317932B2

(12) United States Patent
Torchio et al.

(10) Patent No.: US 11,317,932 B2
(45) Date of Patent: May 3, 2022

(54) STIFFENING DEVICE ADAPTED TO COOPERATE WITH A FLEXIBLE KIDNEY STONE EXTRACTOR

(71) Applicant: Coloplast A/S, Humlebaek (DK)

(72) Inventors: Gerard Louis Florent Torchio, Verrieres le Buisson (FR); Cesare Scoffone, Alba (IT); David Rigotto, Saint Selve (FR)

(73) Assignee: Coloplast A/S, Humlebaek (DK)

( * ) Notice: Subject to any disclaimer, the term of this patent is extended or adjusted under 35 U.S.C. 154(b) by 269 days.

(21) Appl. No.: 16/673,972

(22) Filed: Nov. 5, 2019

(65) Prior Publication Data

US 2020/0078030 A1 Mar. 12, 2020

Related U.S. Application Data

(63) Continuation of application No. 15/518,247, filed as application No. PCT/EP2015/073387 on Oct. 9, 2015, now Pat. No. 10,499,938.

(30) Foreign Application Priority Data

Oct. 14, 2014 (DK) .................................. 14306628.0

(51) Int. Cl.
*A61B 17/221* (2006.01)
*A61B 17/00* (2006.01)
*A61B 17/29* (2006.01)

(52) U.S. Cl.
CPC .... *A61B 17/221* (2013.01); *A61B 2017/0034* (2013.01); *A61B 2017/0046* (2013.01);
(Continued)

(58) Field of Classification Search
CPC .......... A61B 17/221; A61B 2017/2918; A61B 2017/00336; A61B 2017/0034;
(Continued)

(56) References Cited

U.S. PATENT DOCUMENTS 5,569,269 A 10/1996 Hart et al.
7,993,329 B2 * 8/2011 Howell ................ A61B 17/221
606/2.5
(Continued)

FOREIGN PATENT DOCUMENTS

CN 1859874 A 11/2006
CN 101172031 A 5/2008
(Continued)

*Primary Examiner* — Sarah A Simpson
(74) *Attorney, Agent, or Firm* — Coloplast Corp., Coloplast A/S; Nick Baumann

(57) ABSTRACT

A stiffening device is disclosed that is adapted to cooperate with a flexible kidney stone extractor. The stiffening device includes a tube having a lumen sized to receive a part of flexible kidney stone extractor; a diversion member having a channel that is configured to receive a part of the flexible kidney stone extractor; and a connector coupled between the tube and the diversion member. The connector allows the channel of the diversion member to communicate with the lumen of the tube. A proximal portion of the connector is connected to the diversion member and a distal portion of the connector is connected to the tube.

11 Claims, 2 Drawing Sheets

(52) U.S. Cl.
CPC ............... *A61B 2017/00336* (2013.01); *A61B 2017/2901* (2013.01); *A61B 2017/2904* (2013.01); *A61B 2017/2905* (2013.01); *A61B 2017/2918* (2013.01)

(58) Field of Classification Search
CPC .... A61B 2017/0069; A61B 2017/2904; A61B 2017/2905
See application file for complete search history.

(56) References Cited

U.S. PATENT DOCUMENTS

| | | |
|---|---|---|
| 2004/0111082 A1 | 6/2004 | Howell et al. |
| 2005/0096694 A1 | 5/2005 | Lee |
| 2007/0296365 A1 | 12/2007 | Messerly et al. |
| 2008/0296343 A1 | 12/2008 | Schall et al. |
| 2010/0292712 A1 | 11/2010 | Hering et al. |
| 2012/0179146 A1 | 7/2012 | Fan et al. |
| 2012/0323070 A1 | 12/2012 | Danitz et al. |
| 2013/0098966 A1 | 4/2013 | Kostrzewski et al. |
| 2014/0236165 A1 | 8/2014 | Ries et al. |
| 2014/0276967 A1 | 9/2014 | Fischvogt et al. |

FOREIGN PATENT DOCUMENTS

| | | |
|---|---|---|
| CN | 101313864 A | 12/2008 |
| CN | 102711629 A | 10/2012 |
| CN | 103338712 A | 10/2013 |
| CN | 103565489 A | 2/2014 |
| CN | 103732164 A | 4/2014 |
| CN | 104042283 A | 9/2014 |
| CN | 104066390 A | 9/2014 |
| JP | 8505307 T2 | 6/1996 |
| JP | 2003061902 A2 | 3/2003 |
| JP | 2006502760 A | 1/2006 |
| WO | 04110285 A1 | 12/2004 |
| WO | 14039099 A1 | 3/2014 |

* cited by examiner

STIFFENING DEVICE ADAPTED TO COOPERATE WITH A FLEXIBLE KIDNEY STONE EXTRACTOR

The presence of stones in a kidney, or at the start of the ureter below the kidney, is the source of problems or symptoms such as pain, bleeding and infection, and it also poses a risk of the flow of urine becoming blocked, eventually with loss of function of the kidney and then the destruction thereof. It is therefore necessary to remove these stones. Indeed, if treatment is not provided, the patient will continue to have these problems, or will see them recur, and will suffer complications.

There are various methods of treatment. The choice of technique depends principally on the size, location and hardness of the stone. Generally, percutaneous nephrolithotomy is recommended for stones measuring in excess of 1 cm.

Percutaneous nephrolithotomy involves passing directly into the kidney, through the skin and wall of the back, a nephroscope, with which it is possible to see the stone or stones, a lithotripter, which allows the stone or stones to be fragmented, and a stone extractor, which allows these stones to be captured and extracted from the patient.

SUMMARY

The present disclosure relates to an instrument that can be used in situations where a rigid nephroscope has to be used and also in situations where a flexible nephroscope is more suitable.

According to an embodiment of the invention, this instrument can be reversible, that is to say it can be reused in its rigid configuration after it has been used in its flexible configuration, and vice versa.

Disclosed is an extraction device for extracting a foreign body from a patient, this device having:
- a flexible extractor formed by a flexible sheath, by a transmission mandrin arranged in said flexible sheath, by a handle to which a proximal zone of said transmission mandrin is fixed, and by a tool connected to a distal end of said transmission mandrin;
- a stiffening device having a rigid tube in which the flexible sheath of the flexible extractor can be placed; and
- connection means for connecting the flexible extractor to said stiffening device.

Disclosed is also a stiffening device intended to cooperate with a flexible extractor, this stiffening device having a rigid tube able to receive a part of said flexible extractor, and connection means for connecting said stiffening device to said flexible extractor.

According to this disclosure, a surgeon can use the device in a conventional manner in two different configurations. In a first configuration, the device can be used in a rigid nephroscope. In practice, the surgeon generally begins by using this type of nephroscope to remove the largest stones. These rigid nephroscopes are generally short in length, like the device according to the invention, in its rigid configuration. For this reason, the surgeon can work with this device in the way to which he is accustomed with the conventional rigid nephroscopes.

In a second phase, if the surgeon wishes to use a flexible device, particularly in order to explore other calyces of the kidney and/or remove stones or fragments of stones therefrom, the device according to the invention can be transformed into a flexible extractor. It will be noted that a flexible nephroscope conventionally has a greater length than a rigid nephroscope. In one embodiment, this characteristic is respected, such that a surgeon will also be able to work in a conventional way when using the disclosed device in a configuration corresponding to a flexible nephroscope.

According to the disclosure, the surgeon will be able to use a single device that can be flexible or rigid, depending on the needs of the moment. Moreover, he will be able to use this device with the conventional appliances, without having to adapt these. He will also be able to use this device in the same way as the devices to which he is accustomed, which avoids the need for learning new manoeuvres and reduces the attendant risks.

BRIEF DESCRIPTION OF THE DRAWINGS

The present invention and its advantages will be better understood by reference to the detailed description of a particular embodiment and to the attached figures, in which.

DETAILED DISCLOSURE

Figure 1:
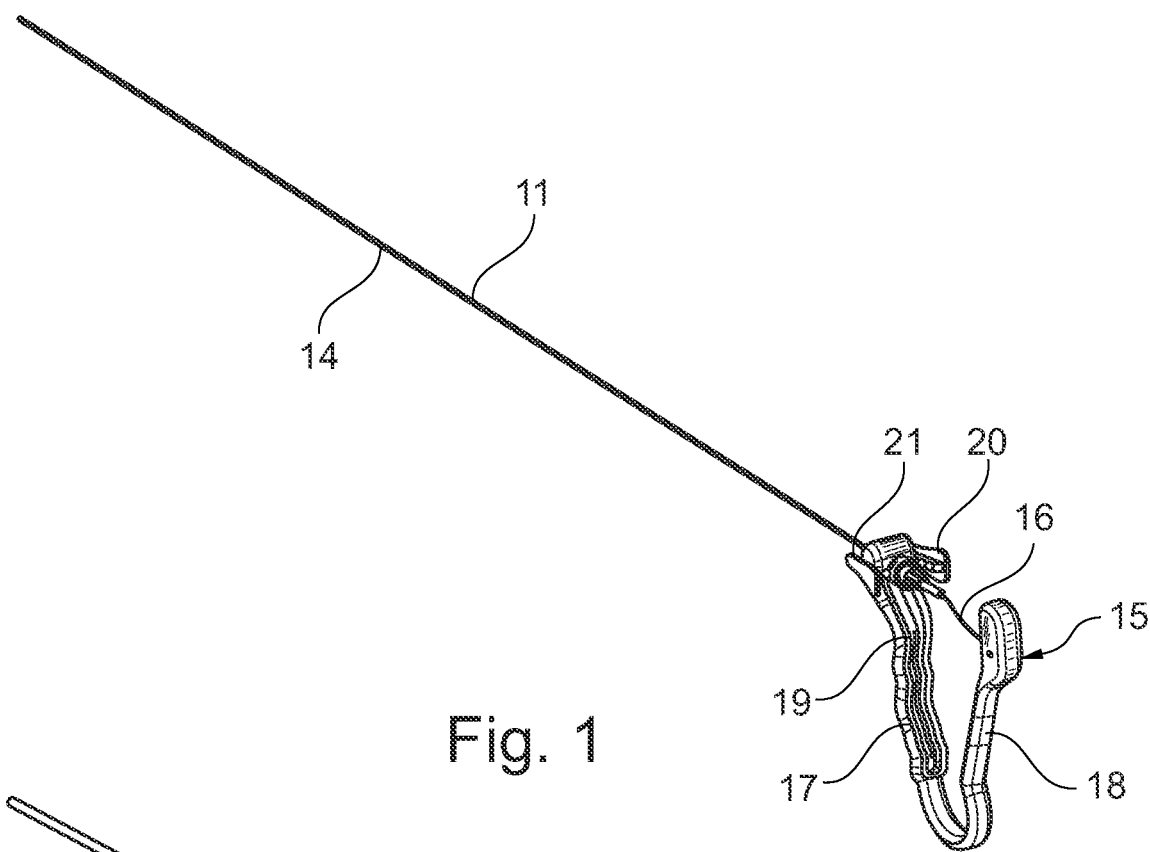
FIG. 1 is a perspective view of a flexible extractor according to one embodiment.
Figure 2:
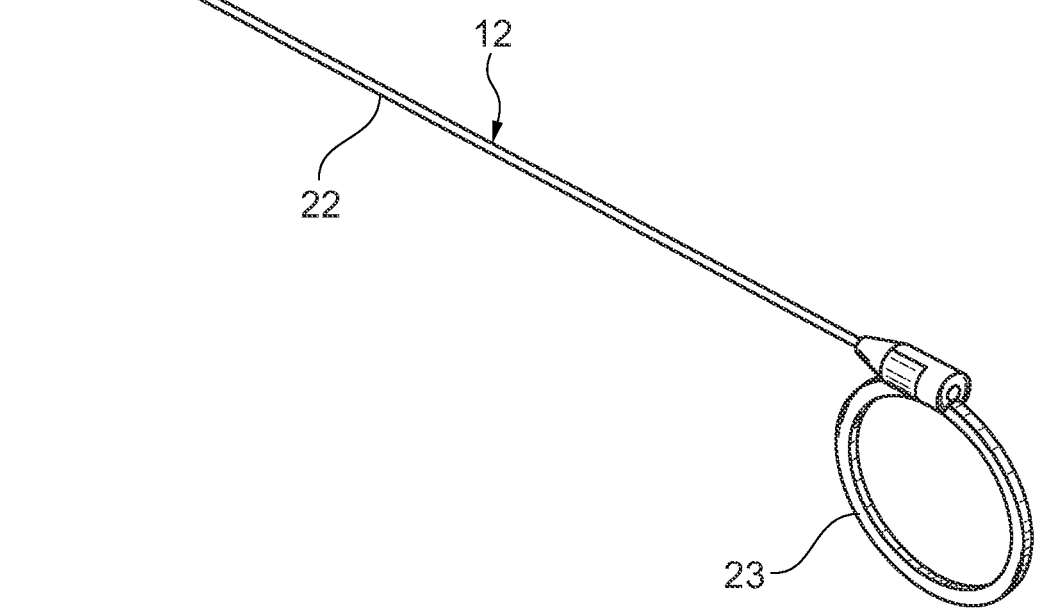
FIG. 2 shows a stiffening device according to one embodiment.

With reference to the figures, disclosed is an extraction device 10 for extracting foreign bodies from a patient, in particular an extraction device for extracting stones from the body of a patient. This extraction device is composed essentially of two elements, namely a flexible extractor 11 and a stiffening device 12. The extraction device 10 according to the invention additionally has connection means 13 for connecting the flexible extractor 11 to said stiffening device 12.

The flexible extractor 11 has a flexible sheath 14 rigidly connected to a handle 15, and a transmission mandrin 16, which is also rigidly connected to the handle 15. The transmission mandrin 16 is flexible and slides in the flexible sheath 14.

The handle 15 has a shape substantially similar to a U and has a distal part 17, to which the flexible sheath is fixed, and a proximal part 18, to which the transmission mandrin 16 is fixed. The distal part 17 and proximal part 18 of the handle can move relative to each other. According to one embodiment, the relative movement of the two parts of the handle is effected by virtue of the elasticity of the material from which this handle is made. This material can advantageously be a polymer such as polyamide, POM (polyoxymethylene), a polycarbonate or ABS (acrylonitrile butadiene styrene). Other suitable materials could also be used. Other methods of assembly can clearly be used, for example assembly with a hinge in the lower part of the U connecting the distal part 17 and proximal part 18 of the handle. This method of assembly also permits a relative movement of the distal and proximal parts of the handle. Many variants of the handle can be used, for example a handle with a syringe-type pusher.

The transmission mandrin 16, at its distal end remote from the handle 15, is rigidly connected to a tool (not shown). According to one embodiment, the tool can be a stone extractor, allowing stones to be grasped and extracted from the body of a patient. Other tools could clearly be used depending on the application.

The transmission mandrin 16 can adopt two extreme positions, namely a retracted position, in which the distal end of the transmission mandrin 16 and the tool too are located inside the flexible sheath 14, and a working position, in which the tool is outside this sheath 14.

According to one embodiment, the handle 15 is designed such that the transmission mandrin 16 is in a retracted position when no force is exerted on the handle.

The handle 15 additionally has a part of the connection means 13 for connecting the flexible extractor 11 to said stiffening device 12. For this purpose, the distal part 17 of the handle has a longitudinal slit 19, the use of which is explained in more detail below. The handle 15 also has two elastic tabs 20, each elastic tab being provided with a lug 21.

According to one embodiment, the proximal end of the transmission mandrin 16 is fixed non-detachably to the handle 15. It is possible to use a non-detachable fastening on account of the flexibility of the transmission mandrin 16. However, this mandrin must be chosen such that it does not buckle when the handle is moved from the retracted position to the working position, while at the same time folding in the area of fastening to the handle.

In one embodiment, the length of the flexible sheath 14 is such that the flexible extractor 11 can be used with the conventional appliances, in particular with a nephroscope or a flexible endoscope. This length is generally between 40 and 120 cm.

The stiffening device 12 essentially comprises a rigid tube 22, a diversion member 23, and a part of the connection means 13 for connecting the flexible extractor 11 to said stiffening device 12. The rigid tube 22 has an inner channel 24 with a diameter such that the flexible sheath 14 of the flexible extractor can be introduced therein. This rigid tube 22 advantageously has a size corresponding to the rigid nephroscopes traditionally used. The length of the rigid nephroscopes is generally between 20 and 40 cm for an internal diameter of between 1 and 6 mm. The rigid tube can be made of metal or of polymer, the metal being, for example, a medical-grade stainless steel such as 316 type steel or a suitable alloy, the polymer being, for example, a polymer reinforced with carbon fibres, glass fibres or Kevlar. Other suitable materials can also be used.

In one embodiment as illustrated, the diversion member 23 is formed by a ring, the inner channel 24 having a size sufficient to allow the passage of the sheath 14 of the flexible extractor 11.

The length of the ring, or the perimeter of the diversion member 23 when the latter has a circular shape, is substantially equal to the difference between the length of the rigid tube 22 and the length of the flexible sheath 14, as is explained in more detail below.

Figure 3:
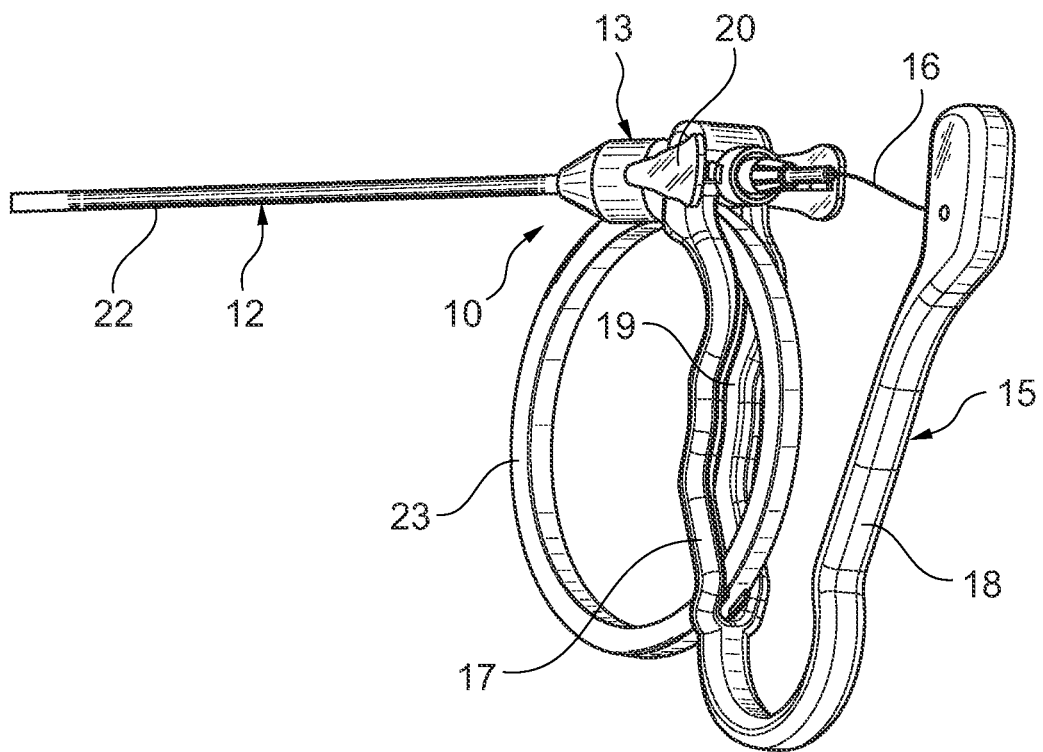
FIG. 3 is a perspective view of the extraction device according to one embodiment.
Figure 4:
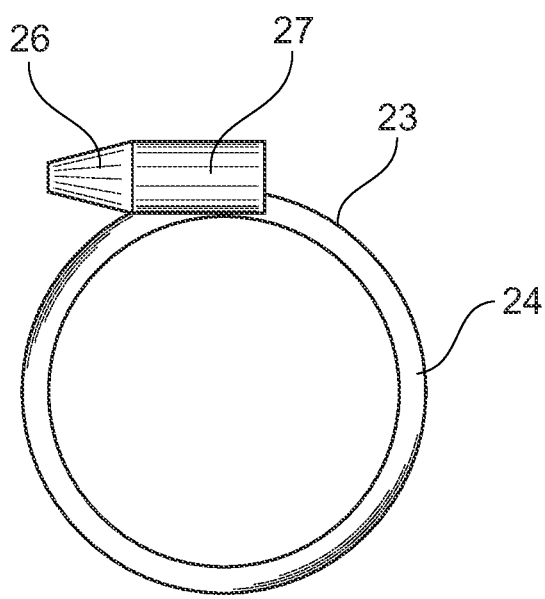
FIG. 4 shows a detail of an element according to one embodiment.
Figure 5:
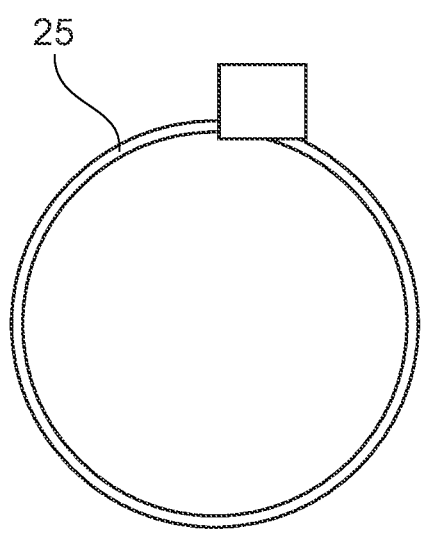
FIG. 5 shows another detail of the device according to one embodiment.

The diversion member 23, as illustrated in FIGS. 3 to 5, has a cover 25 permitting access to the inner channel 24. This can make it easier to place the flexible sheath 14 in this diversion member 23.

According to one embodiment, the diversion member 23 has a thickness and a position which are such that a part of this member can be placed in the longitudinal slit 19 of the handle 15. It should be noted that this diversion member could be placed in a position separate from the handle 15 such that these two elements are not in contact with each other.

The stiffening device 12 has a holding member 26 in which the rigid tube 22 is fixed. This holding member is provided with notches 27 designed to cooperate with the lugs 21 of the handle 15.

It is well known to a person skilled in the art that, when a surgeon seeks to remove a foreign body from a patient, in particular a stone from a kidney of the patient, he can use a technique called percutaneous nephrolithotomy, as has been mentioned above. In this technique, a channel is formed through the patient's back to the kidney from which the stone is to be removed. In most cases, the surgeon uses a rigid nephroscope to access the stones situated approximately in the continuation of the nephroscope. For the stones that are located elsewhere than in the continuation of the nephroscope, for example in other calyces of the kidney, the surgeon uses a flexible nephroscope.

According to the present disclosure, the extraction device 10 can first of all be used as a conventional rigid nephroscope. To this end, the flexible sheath 14 is first of all introduced into the inner channel 24 of the diversion member 23. To do this, the flexible sheath can simply be pushed into the diversion member 23, its shape being such that the sheath does not directly enter the rigid tube 22 but instead first of all passes into the inner channel 24 before emerging from this channel and entering the rigid tube 22. If the diversion member 23 has a cover 25, the latter may optionally be removed, if necessary, to facilitate the placement of the flexible sheath 14.

This flexible sheath 14 is then pushed to its extreme position in which the tool placed at the end of the transmission mandrin 16 of the flexible extractor 11 is arranged near the free end of the rigid tube 22.

In this position, the various components forming the connection means 13 are engaged in such a way as to keep the flexible extractor rigidly connected to the stiffening device. More specifically, the diversion member 23 of the stiffening device 12 is engaged in the longitudinal slit 19 of the handle 15 of the flexible extractor. The lugs 21 formed on the elastic tabs 20 of the handle 15 are engaged in the notches 27 of the holding member 26. In this way, the flexible extractor 11 and the stiffening device 12 are rigidly connected and can be used in the same way as a conventional rigid extractor. The actuation of the handle 15 has the effect of moving the transmission mandrin 16, which permits actuation of the tool arranged at the end of this transmission mandrin. The elasticity of the handle is such that, in the absence of force applied to this handle, the tool is arranged inside the flexible sheath 14 and inside the rigid tube 22.

When the surgeon wishes to use the extraction device 10 in a flexible nephroscope, he spreads the elastic tabs 20 apart, which has the effect of freeing the lugs 21 of the holding member 26. He removes the diversion member 23 from the longitudinal slit 19 of the handle 15 and pulls the flexible sheath 14 from the rigid tube 22. In this configuration, the entire length of the flexible sheath 14 can then be used, thereby making it possible to use this extractor 11 with conventional flexible nephroscopes.

If the surgeon wishes to reuse the extraction device 10 in its configuration as rigid extractor, it suffices to reintroduce the flexible sheath 14 into the diversion member 23 and reposition this diversion member 23 in the longitudinal slit 19 of the handle 15 and reposition the lugs 21 on the holding member 26.

The present disclosure thus makes available, in a single extraction device, a configuration corresponding to a flexible nephroscope and a configuration corresponding to a rigid nephroscope. In one embodiment, this device is totally reversible, which allows the surgeon to choose at any moment the configuration that is the most appropriate to the situation. The device according to the disclosure is also dimensioned in such a way as to correspond to the dimensions of the conventional flexible or rigid nephroscopes, which means that the device according to the invention can be used with conventional appliances without, on the one hand, other appliances having to be developed and, on the other hand, without the surgeon having to become familiarized with other instruments or other ways of working. However, it is possible to provide an extraction device that does not have a diversion member 23. In this case, the length of the device according to the invention is substantially the same in its flexible configuration and in its rigid configuration.

In the example shown, the connection means 13 are formed in particular by the handle 15 and by the diversion device 23. It is also possible that this handle and this diversion device are independent of each other and do not form part of the connection means.

It is also possible to use non-reversible connection means. In this case, the connection means can, for example, be broken at a break zone so as to separate the stiffening device from the flexible extractor, without any possibility of reconnecting the stiffening device to this flexible extractor.

The present disclosure describes a use in which stones are removed from the kidneys of a patient. The same principle could be applied to other foreign bodies to be removed from a patient.

What is claimed is:

1. A stiffening device adapted to cooperate with a flexible kidney stone extractor, the stiffening device comprising:
   a tube having a lumen sized to receive a part of the flexible kidney stone extractor;
   a diversion member having a channel that is configured to receive a part of the flexible kidney stone extractor;
   a connector coupled between the tube and the diversion member, where the connector allows the channel of the diversion member to communicate with the lumen of the tube; and
   a cover sized to couple to the diversion member and close off access to the channel;
   wherein a proximal portion of the connector is connected to the diversion member and a distal portion of the connector is connected to the tube.

2. The stiffening device of claim 1, wherein the tube comprises one of a metal tube and a reinforced polymer tube adapted to access a kidney percutaneously through skin of a patient.

3. The stiffening device of claim 1, wherein, when the stiffening device is coupled with the flexible kidney stone extractor, a path length of the channel in the diversion member is substantially equal to a difference between a length of a sheath of the flexible kidney stone extractor and a length of the tube.

4. The stiffening device of claim 1, wherein the stiffening device is adapted to convert the flexible kidney stone extractor to a rigid nephroscope by accommodating an excess portion of a length of the flexible kidney stone extractor within the channel of the diversion member.

5. A stiffening device useable with a flexible kidney stone extractor, the stiffening device comprising:
   a tube having a lumen sized to receive a part of the flexible kidney stone extractor;
   a diversion member having a channel that is configured to receive a part of the flexible kidney stone extractor;
   a connector coupled between the tube and the diversion member, where the connector provides a communication path that couples the channel of the diversion member with the lumen of the tube; and
   a cover sized to couple to the diversion member and close off access to the channel;
   wherein the tube comprises one of a metal tube and a reinforced polymer tube having a stiffness adapted to access a kidney percutaneously through skin of a patient.

6. The stiffening device of claim 5, wherein a proximal portion of the connector is connected to the diversion member and a distal portion of the connector is connected to the tube.

7. The stiffening device of claim 5, wherein a distal portion of the connector includes a holding member for removable attachment of the tube to the connector.

8. The stiffening device of claim 5, wherein the diversion member is circular.

9. An attachment provided with a flexible kidney stone extractor, where the flexible kidney stone extractor has a sheath surrounding a wire and a stone extraction tool attachable to the wire, and the sheath has a sheath length that is adapted to allow the flexible kidney stone extractor to access calyces of a kidney, the attachment comprising:
   a tube having a lumen sized to receive the sheath of flexible kidney stone extractor;
   a housing having a channel that is configured to receive a part of the sheath of the flexible kidney stone extractor;
   a connector coupled between the tube and the housing, where the connector provides a communication path that couples the channel of the housing with the lumen of the tube; and
   a cover sized to couple to the housing and close off access to the channel,
   wherein a stiffness of the tube is greater than a stiffness of the sheath of the flexible kidney stone extractor such that the attachment, when coupled with the flexible kidney stone extractor, converts the flexible kidney stone extractor to a rigid nephroscope that is adapted to access a kidney percutaneously through skin of a patient.

10. The stiffening device of claim 9, wherein, when the attachment is coupled with the flexible kidney stone extractor, the sheath and the wire are disposed within the tube and the channel formed in the housing to prevent the wire from extending beyond a distal end of the tube.

11. A stiffening device adapted to cooperate with a flexible kidney stone extractor, the stiffening device comprising:
   a tube having a lumen sized to receive a part of the flexible kidney stone extractor;
   a diversion member having a channel that is configured to receive a part of the flexible kidney stone extractor; and
   a connector coupled between the tube and the diversion member, where the connector allows the channel of the diversion member to communicate with the lumen of the tube;
   wherein a proximal portion of the connector is connected to the diversion member and a distal portion of the connector is connected to the tube;
   wherein, when the stiffening device is coupled with the flexible kidney stone extractor, a path length of the channel in the diversion member is substantially equal to a difference between a length of a sheath of the flexible kidney stone extractor and a length of the tube.

\* \* \* \* \*